United States Patent [19]

Nakajima et al.

[11] Patent Number: 5,246,968

[45] Date of Patent: Sep. 21, 1993

[54] GLUTAMATE RECEPTOR INHIBITOR

[75] Inventors: Terumi Nakajima; Yoshio Aramaki; Tadashi Yasuhara, all of Tokyo; Tsutomu Higashijima, Saitama; Nobufumi Kawai, Tokyo; Akiko Miwa, Tokyo; Masanori Yoshioka, Kyoto, all of Japan

[73] Assignees: Takeda Chimical Industries, Ltd.; Tokyo Metropolitan Institute for Neurosciences, Tokyo, Japan

[21] Appl. No.: 908,563

[22] Filed: Jun. 30, 1992

Related U.S. Application Data

[63] Continuation of Ser. No. 829,630, Jan. 31, 1992, abandoned, which is a continuation of Ser. No. 652,497, Feb. 11, 1991, abandoned, which is a continuation of Ser. No. 113,149, Oct. 27, 1987, abandoned.

[30] Foreign Application Priority Data

Feb. 3, 1987 [JP] Japan .................. 62-23147
Mar. 6, 1987 [JP] Japan .................. 62-52296

[51] Int. Cl.$^5$ ............................................. A61K 31/16
[52] U.S. Cl. ................................. 514/616; 564/153
[58] Field of Search ................ 564/153; 424/98; 514/616

[56] References Cited

U.S. PATENT DOCUMENTS 4,855,405 8/1989 Yoshioka et al. .............. 530/300

FOREIGN PATENT DOCUMENTS 156540 10/1985 European Pat. Off. .............. 424/98

OTHER PUBLICATIONS

Kawai et al., *Brain Research*, vol. 278 (1983) 346-9.
Kawai et al., *Brain Research*, vol. 247 (1982) 169-171.
Kawai et al., *Microelectrophoretic Investigations of Mammalian Central Transmitters*, (Aug. 1983).
Kawai; XIII$^{ime}$ Conference in Neurobiologic de Gif., Nov. 1983.
Kawai et al, *CNS Receptors: From Molecular Pharmacology to Behavior*, vol. 37 (1983), pp. 221-227.
Abe et al., *J. physiol*, vol 339 (1983), pp. 243-252.
Kawai et al, *Biomedical Research*, vol. 3(3)(1982), pp. 353-355.
Aramehi et al., Proc. Japan Scad., 62, Ser. B. (1986), 359-362.

*Primary Examiner*—Allen J. Robinson
*Assistant Examiner*—B. Burn
*Attorney, Agent, or Firm*—Antonelli, Terry, Stout & Kraus

[57] ABSTRACT

A compound having glutamate receptor inhibitor activity represented by the formula:

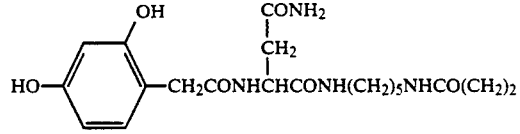

$$NH[(CH_2)_mNH]_p(CH_2)_nNHR$$

where R represents a hydrogen atom or a group of the formula:

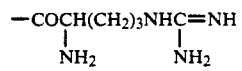

m and n each represents an integer of 3 or 4 and p represents an integer of 0 or 1, or a salt thereof is provided. The compounds are useful for an insecticide.

4 Claims, 5 Drawing Sheets

GLUTAMATE RECEPTOR INHIBITOR

This application is a continuation of application Ser. No. 07/829,630, filed Jan. 31, 1992, abandoned which is a continuation of application Ser. No. 07/652,497, filed Feb. 11, 1991, abandoned, which is a continuation of Ser. No. 07/113,149, filed Oct. 27, 1987, abandoned.

The present invention relates to a new compound or salts thereof having glutamate receptor inhibiting action, and an insecticidal composition containing the same.

Arthropods such as insects are paralyzed when bitten by Arachnoidea, e.g., *Nephila clavata* and *Nephila maculata*, and then fall prey to the spiders. It has been considered, therefore, that there exists in the body of such spider a chemical substance that paralyses the nerve of arthropods such as insects. Isolation of chemical substances which paralyze the nerve of arthropods such as insects from *Nephila clavata* and the like has been attempted (for instance, U.S. Pat. Application No. 707,381 now U.S. Pat. No. 5,190,174 determined to a certain extent, and the nervous paralysis is confirmed to be due to the glutamate receptor inhibiting action of the substances. For example, $N^1$-(2,4-dihydroxyphenylacetylasparaginyl)-$N^5$-(arginyl-cadaverinoalanyl)-cadaverine is disclosed in "Proceedings of the Japan Academy", 62, Ser. B. 359, 1986 by the same authors as those of the present invention (structure disclosed is later amended to the same as given in the present) and (2,4-dihydroxyphenylacetylasparaginyl)-polyamine-arginyl wherein polyamine is $-NH(CH_2)_3NH(CH_2)_3NH(CH_2)_5NH-$ in Chemical Abstracts, 105: 186106d, 1986.

The present inventors further studied compounds obtained from the venom glands of the spiders which paralyze the nerve of arthropods and determined the chemical structure of the compounds. After additional research, the present inventors selected those compounds which have glutamate receptor inhibiting activity and contain an amino acid residue in the molecules, and succeeded in providing an insecticidal composition containing the same.

The present insecticidal composition contains a compound or a salt thereof represented by the formula [I] below:

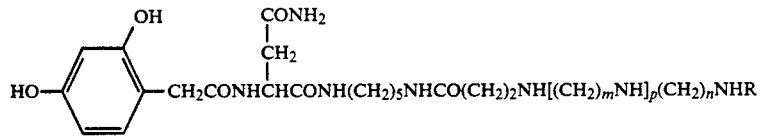

where R represents a hydrogen atom or a group of the formula:

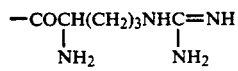

(which is referred to as "Arg" hereinbelow) m and n each represents an integer of 3 or 4, and p represents an integer of 0 or 1.

The salt of the compound [I] include salt with inorganic acids or organic acids. Examples of the inorganic acid salts include hydrochorides, sulfates, carbonates and nitrates. Examples of the organic acid salts include formates, acetates, propionates, oxalates, succinates, benzoates and p-toluenesulfonates. The α-amino acid constituting the compound [I] may be either of L-form, D-form or of DL-form, the former being preferable.

The compound [I] is produced from *Nephila clavata* (Joro spider) by the process which involves extraction and purification. It may also be produced by chemical synthesis. The extraction from *Nephila clavata* may be accomplished by treating the body of *Nephila clavata*, preferably the venom glands previously separated therefrom, with an extracting solvent. It is preferable to disintegrate the body, preferably venom glands, previously prior to extraction. The disintegrate should preferably be carried out in the extracting solvent. The disintegration may be accomplished by using an atomizer or homogenizer or an ultrasonic disintegrator.

The extracting solvent may be an aqueous solvent such as water, aqueous electrolyte solution or a mixed solvent of water and water-miscible organic solvent. The aqueous electrolyte solution includes solution of sodium chloride, ammonium chloride or sodium sulfate. The aqueous electrolyte solution has concentration of 0–1.5% (w/v), preferably 0.3–0.5% (w/v). The water-miscible organic solvent includes alcohols such as methanol, ethanol and propanol; nitriles such as acetonitrile; and ketones such as acetone. The most desirable extracting solvent is a mixed solvent of water and acetonitrile.

The extraction may be accomplished simply by leaving a mixture with the solvent to stand for a long period of time. The extraction may also be accomplished in a short period of time by using an ordinary stirrer or centrifuge. Extraction by a centrifuge is advantageous because the extract layer can be easily separated from the residues. Centrifugation should be performed at 1,000–100,000 rpm for 5 minutes to 3 hours.

The tracing of the active component may be conveniently achieved by measuring the excitatory postsynaptic potential (EPSP) of the synapse at the neuromuscular junction of the walking legs of a lobster (*Panulirus japonicus*). (The measuring method will be mentioned later.) The results of the measurement indicate that the active component has moved to the extract layer. The active component stays in the water layer despite any attempt to transfer it to a common organic solvent such as ethyl acetate and methylene chloride.

The extract obtained as mentioned above is subsequently purified. Prior to purification, it is desirable to remove the solvent used for the extraction. The removal of the solvent may be accomplished in the usual way, e.g., by distillation under reduced pressure or lyophilization. The purification may be accomplished by means of gel filtration, treatment with ion-exchange resin, preparative silica gel thin-layer chromatography, or high-performance liquid chromatography (HPLC for short). The latter is preferable for the separation and purification of the extract containing a large number of active components. The use of a reversed-phase partition column is desirable for HPLC. The solvent for separation and purification may be selected from the aqueous solvents used for the extraction. In the case of HPLC with a reversed-phase partition column, the column should preferably be 200–500 mm long and 4–10 mm in inside diameter and the resin should preferably be 3–10 μm in diameter. For good separation, the column temperature should be at room temperature to 70° C. and the eluent should be a mixed solvent of dilute hydrochloric acid and acetonitrile.

The thus separated and purified active component or the compound [I] of the present invention may be stored after lyophilizing.

The thus obtained compound [I] includes two or more analogous compounds, each of which is identified as an independent compound by silica gel thin-layer chromatography, gel filtration, and electrophoresis. In actuality, four compounds Ia, Ib, Ic and Id are obtained from Nephila clavata and three compounds Ie, If and Ig from Nephila maculata, as shown in the Examples described hereinafter.

The chemical structure of the compound [I] is determined by means of amino acid analysis, $^1$H-NMR, $^{13}$C-NMR, mass spectrum, IR and UV.

The compounds Ib, Ic, Id and Ig have the structure shown below:

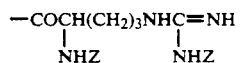

where m, n and p are as defined above; R' represents a hydrogen atom or a group of the formula below:

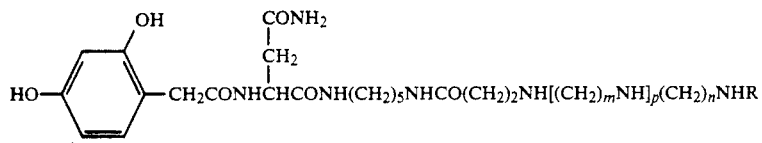

where Bz represents a benzyl group; and Z represents a benzyloxycarbonyl group.

The compound [I] produced by the chemical process may be isolated and purified by the known methods such as extraction, concentration, gel filtration, treatment with ion-exchange resin, preparative silica gel thin-layer chromatography and high-performance liquid chromatography. Isomers resulting from the asymmetric carbon atom may be separated from one another in the usual way.

In the accompanying drawings.

[I]

HO—⟨⟩—CH$_2$CONHCHCONH(CH$_2$)$_5$NHCO(CH$_2$)$_2$NH[(CH$_2$)$_m$NH]$_p$(CH$_2$)$_n$NHR with OH, CONH$_2$, CH$_2$ substituents Ib R = H, m = 3, n = 3, p = 1 or
    R = H, m = 3, n = 4, p = 1
Ic R = H, m = 4, n = 3, p = 1
Id R = Arg, m = 3, n = 4, p = 1 or
    R = Arg, m = 4, n = 3, p = 1 and
Ig R = Arg, n = 4, p = 0

The compound [I] may also be synthesized according to the following reactions.

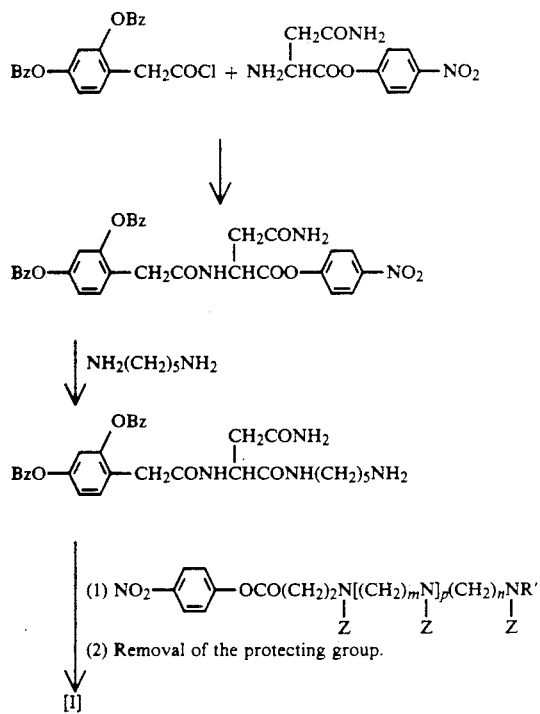

Ib, Ic, Id and Ig in D$_2$O.

Figure 4:
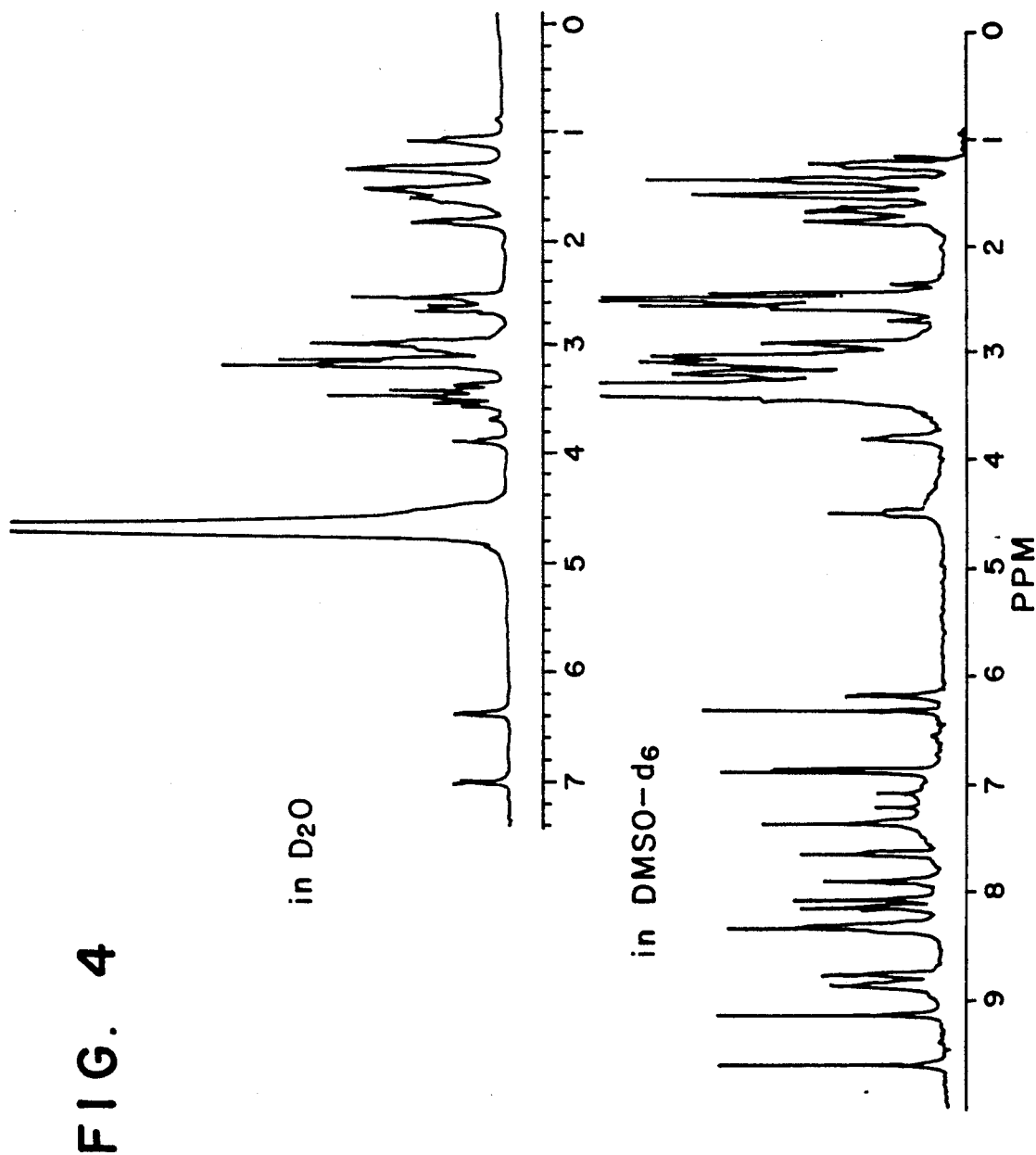

FIG. 4 shows proton NMR spectra of the compound Ig in D$_2$O and d$_6$-DMSO.

Figure 5:
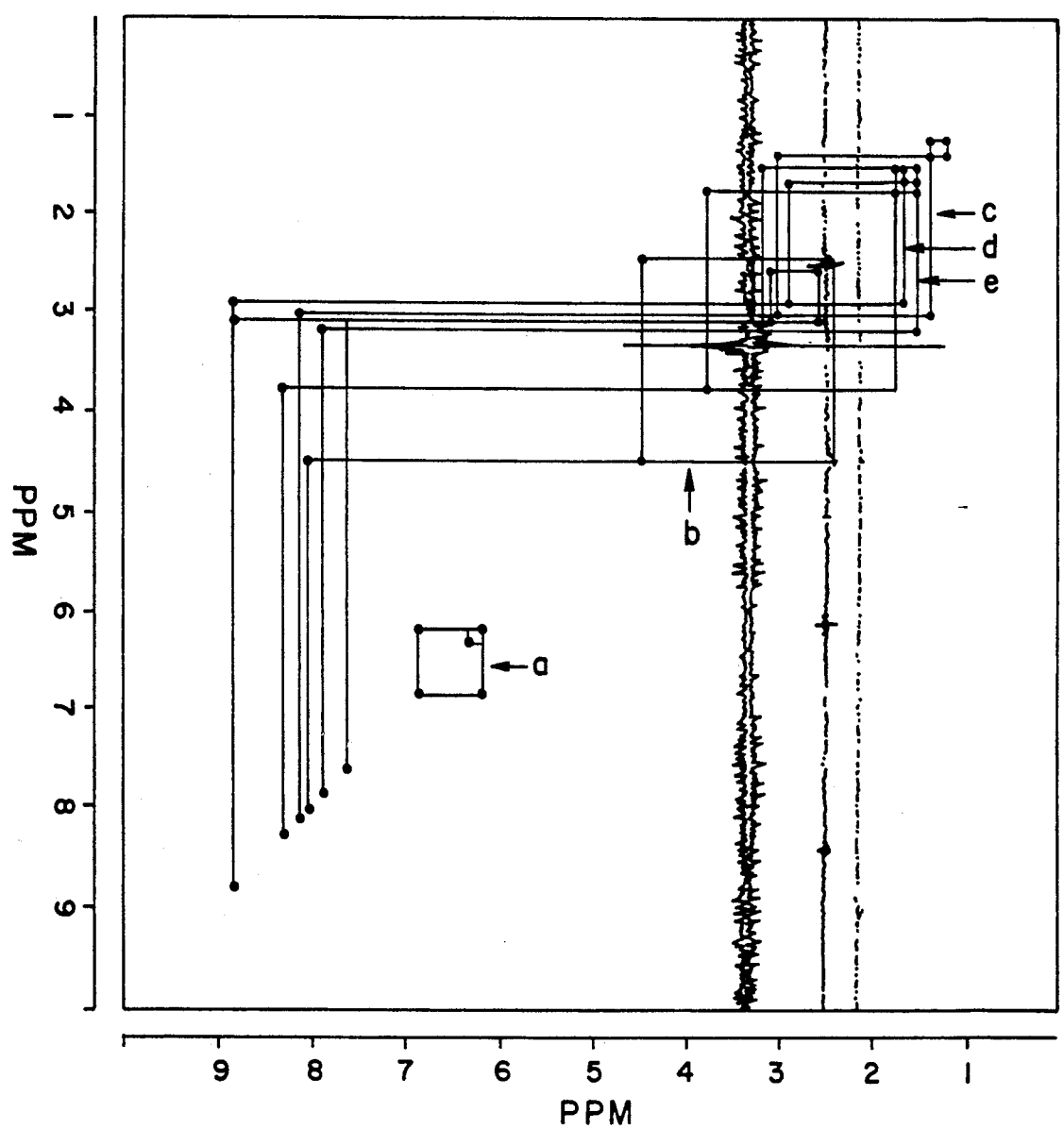

FIG. 5 shows proton-COSY-NMR spectrum of the compound Ig in d$_6$-DMSO.

The present compound is confirmed to be different from a compound obtained from Arachnoidea in U.S. patent application Ser. No. 707,381, now U.S. Pat. No. 5,190,174 mentioned above whose structure is not known yet on the basis of such physico-chemical properties as Rf, UV, NMR and amino acid analysis, although some of the present compounds are obtained from Arachnoidea.

Bioassay of the active component is carried out by using the nerve-muscle synapse of Palinusus japonicus walking legs. Stretcher muscles of Palinusus japonicus walking legs are exposed to record the potential using glass microelectrodes filled with aqueous 3M KCl solution.

The activity of the inhibitory substance is determined by either (1) or (2) below.

(1) Electric stimulation is given through a suction electrode to the excitatory nerve of the stretcher muscle discrete into a single axon. Excitatory nerve stimulations give rise to release of glutamic acid, which binds to the glutamate receptor, resulting in the development of excitatory postsynaptic potential (EPSP) of 3 to 5 mV in the postsynaptic membrane. The glutamate receptor inhibitor decreases by 50% or more or suppresses the EPSPs.

(2) A glass microelectrode filled with glutamic acid (1M, pH 8), is positioned close to the nerve-muscle synapse. Inward current of about $1 \times 10^{-9}$ A to the microelectrode is applied to until about 1M glutamic acid is ejected electrophoretically. As a result, 3 to 5 mV depolarized potential (glutamate potential) is generated in the postsynaptic membrane, the potential being in proportion to the intensity of the current applied to. The glutamate receptor inhibitor decreases by 50% or more or supresses the glutamic acid potential.

The insecticidal composition of the present invention has a high insecticidal activity and produces a satisfactory insecticical effect with a low dosage. In addition to this economical advantage (low dosage), it has another advantage of having very low mammalian toxicity, and fish toxicity and a small adverse influence to the environment. Therefore, it can be used effectively to control pests injurious to hygiene, animals and plants, and forests. The composition may be applied to animals and plants so that it comes into direct contact with pests or it is taken by pests. In other words, the compound [I] as the major ingredient of the composition of the present invention is safe and effective when used for pest control in agriculture.

The insecticidal composition of the present invention which contains the compound [I] is effective against those injurious insects belonging to Lepidoptera such as *Spodoptera litura*, *Plutella xylostella*, *Pierisrapae orucivora*, *Chilo suppressalis*, *Plusia nigrisigna*, *Halicoverpa assulta*, *Leucania separata*, *Mamestra brassicae*, *Adoxophyes orana*, *Syllept derogata*, *Cnaphalocrocis medinalis*, *Phthorimaea operculella*, *Hyphautria cunea* and *Lymantria dispar*; those injurious insects belonging to Coleoptera such as *Epilachna vigintioctopunctata*, *Aulacophora femoralis*, *Phyllotreta striolata*, *Oulema oryzae*, *Echinocnemus squameus*, *Leptinotorsa decemlineata*, *Lissorphopterus oryzophilus* and *Anthonomus grandis*; those injurious insects belonging to Diptera such as *Musca domestica*, *Culexpipiens pallens*, *Culex pipiens molestus*, *Tabanus trigonus*, *Hylemya antiqua* and *Hylemya platura*; those injurious insects belonging to Orthoptera such as *Locusta migratoria*, *Gryllotalpa africana*, *Blattella germanica* and *Periplaneta fuliginosa*; and nematodes such as *Aphelenchoides besseyi*.

The insecticidal composition of the present invention can be used in the form of emulsion, oil solution, wettable powder, dust, granule, tablet, aerosol and ointment according to the intended use. To prepare these formulations, one kind or more of the compound [I] is dissolved or dispersed in a proper liquid carrier or mixed with or adsorbed on a proper solid carrier. Preferred formulations are emulsion, wettable powder, dust and granule. These formulations may be prepared in the known way by incorporating, if necessary, an emulsifier, dispersing agent, spreader, penetrant, wetting agent, thickener, stabilizer and the like.

The insecticidal composition of the present invention contains the compound [I] in various amounts depending on the intended use. The content ranges from 0.00001 to 10% by weight in the case of emulsion and wettable powder, from 0.0000001 to 1% by weight in the case of oil solution and dust, and from 0.000001 to 5% by weight in the case of granule. Prior to application, the emulsion or wettable powder should be diluted for example, (100 to 100000 times) with water.

The liquid carrier for the insecticidal composition of the present invention is water or water-soluble solvent which includes alcohols, e.g., methyl alcohol, ethyl alcohol and ethylene glycol, ketones, e.g., acetone and methyl ethyl ketone, and ethers, e.g., dioxane, tetrahydrofuran, and cellosolve. These solvents may be used alone or in combination with one another. The amount of the liquid carrier in the insecticidal composition varies from one formulation to another. It ranges from 5 to 99.99% by weight.

The solid carrier includes vegetable powder, e.g., soybean powder, tobacco powder, and wood powder, mineral powder, e.g., clays such as kaolin, bentonite and acid clay, talcs, such as agalmatolite powder and silicas such as diatomaceous earth and mica powder, alumina, sulfur powder and active carbon. The carrier may be used alone or in combination with one another. The amount of the solid carrier in the insecticidal composition varies from one formulation to another but ranges from 90 to 99.999999% by weight, preferably from 95 to 99.999999% by weight.

The emulsifier, spreader, penetrant, dispersing agent, etc. contained in the insecticidal composition of the present invention are selected from surface active agents which includes soaps, polyoxyalkylaryl esters, e.g., Nonal ® made by Takemoto Yushi Co., Ltd., alkyl sulfates, e.g., Emal ®-10 and Emal ®-40 made by Kao-Atlas Co., Ltd., alkyl sulfonates, e.g., Neogen ® and Neogen-T ® made by Daiichi Kogyo Seiyaku Co., Ltd.; Neopelex ® made by Kao-Atlas Co., Ltd., polyoxyethylene glycol ethers, e.g., Nonipol ®-85, Nonipol ®-100, and Nonipol ®-160 made by Sanyo Kasei Co., Ltd., and polyhydric alcohol esters e.g., Tween ®-20 and Tween ®-80 made by Kao-Atlas Co., Ltd. The amount of these surface active agents varies from one formulation to another, but 1–20% by weight, preferably 3–10% by weight, in the case of emulsion; 3–30% by weight, preferably 5–20% by weight, in the case of wettable powder; and 0–10% by weight, preferably 0.1–5% by weight, in the case of dust and granule.

The compound [I] may be used in combination with any other insecticide, e.g., pyrethrin-, organophosphate-, carbamate- and natural-insecticides, miticide, nematicide, herbicide, plant hormone, plant growth regulator, fungicide, e.g., copper-, organochlorine-, organosulfur- and phenol-fungicides, synergist, attractant, repellent, colorant and fertilizer in such an amount that does not impair the insecticidal activity of the compound [I].

The insecticidal composition of the present invention which contains the compound [I] may be used in the same way as the ordinary insecticidal composition. Namely, it is used for seedling box treatment, foliage application, body application, water treatment and soil treatment. The dosage may vary according to the timing, place and method of application. The usual dosage is 0.1 mg to 10 g, preferably 1 mg to 5 g (in terms of active ingredient) per hectare.

Glutamate receptor inhibiting action is irreversible and remains even after being washed with water. This indicates that the compound [I] of the present invention combines with the glutamate receptor by far stronger than any other known similar receptors. Therefore, the compound [I] of the present invention is expected to be useful for the separation, structure elucidation and local analysis of the glutamate receptor, if it is properly labelled. Moreover, it is also expected to be used to elucidate the mechanism of memory and the cranial nerve diseases with which glutamic acid is associated.

EXAMPLE 1

Figure 1:
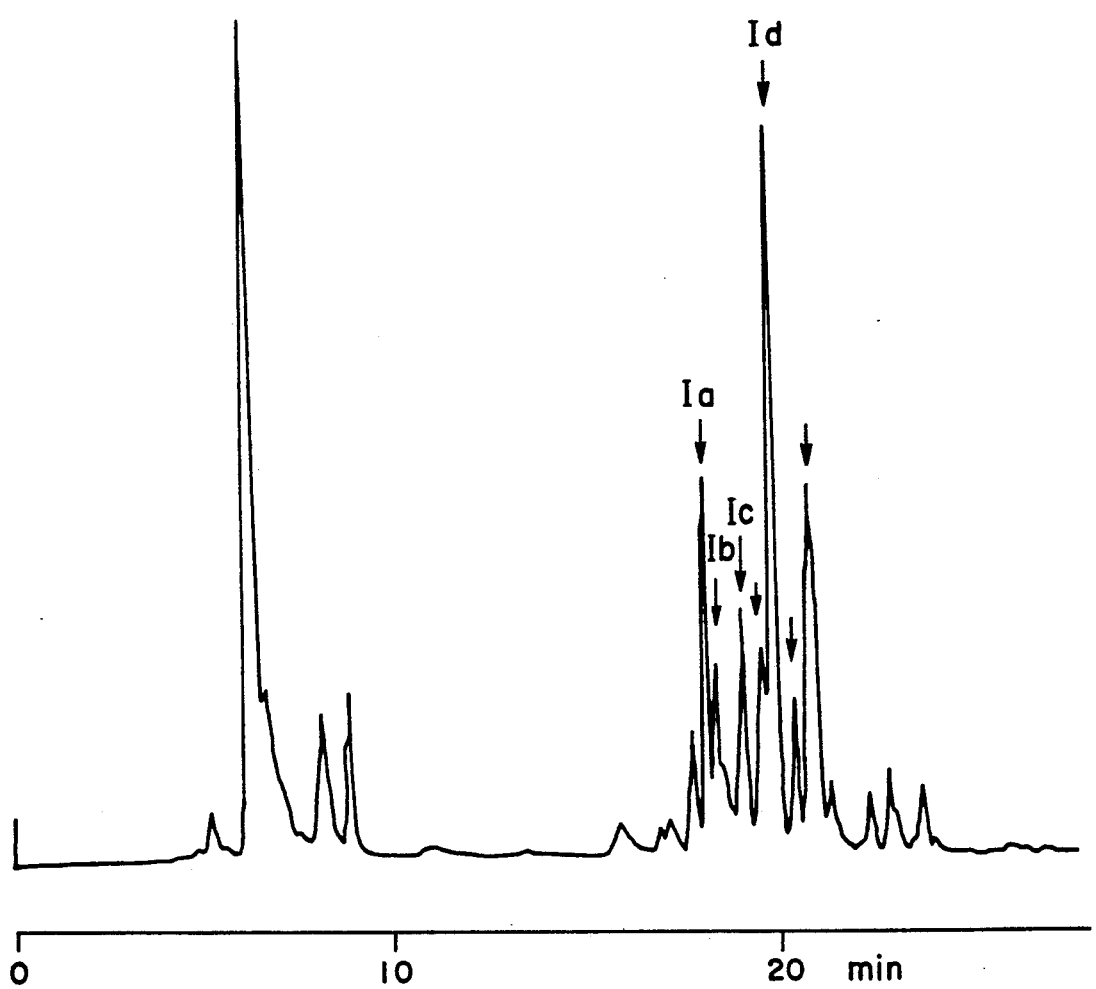
FIG. 1 shows a chromatogram of a sample obtained from Nephila clavata.

Five pieces of venom glands collected from 2.5 heads of *Nephila clavata* collected in Japan were homogenized for 5 minutes in a glass homogenizer containing 1 ml of 60% aqueous acetonitrile (acetonitrile: water=60:40 v/v). The homogenate was centrifuged at 5,000 rpm for 10 minutes. The supernatant liquid was lyophilized. The lyophilized substance was dissolved in 10 μl of water, and the solution subjected to high-performance liquid chromotography (HPLC for short) with a reversed-phase partition column (TSK gel ODS-120 T) made by Toyo Soda Co., Ltd. The column is 250 mm long and 4.6 mm in inside diameter, and the resin is 5 μm in diameter. The column temperature was kept at 40° C. and the elution system employed was a linear concentration gradient using a mixed solvent of 0.02% hydrochloric acid and acetonitrile from 0.02% hydrochloric acid alone to 60% (v/v) acetonitrile, in such a manner that the content of acetonitrile increased at an increment of 1% (v/v) every minute. The flow rate of the eluent was 500 μl/min. The resulting chromatogram is shown in FIG. 1. Four discrete compounds were obtained, which eluted in the order of Ia, Ib, Ic and Id.

EXAMPLE 2

Figure 2:
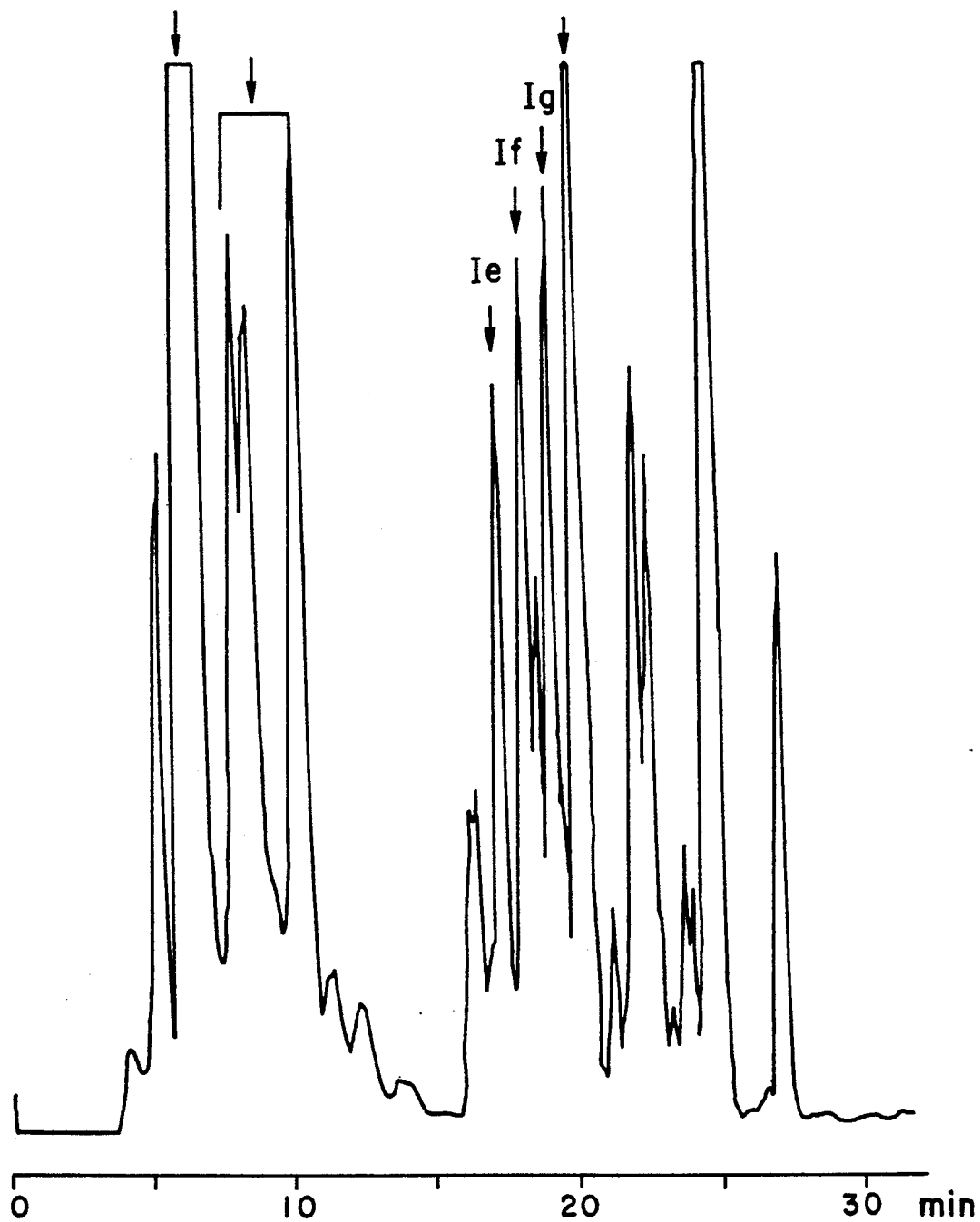
FIG. 2 shows a chromatogram of a sample obtained from Nephila maculata.

The same procedure as in Example 1 was repeated to *Nephila maculata* collected in Papua New Guinea to obtain the chromatogram shown in FIG. 2. There were obtained three independent compounds, which eluted in the order of Ie, If and Ig.

EXAMPLE 3

Half a gram of venom glands collected from 200 heads of *Nephila clavata* in Japan was homogenized for 5 minutes in a glass homogenizer containing 10 ml of 60% aqueous acetonitrile (acetonitrile: water=60:40 v/v). The homogenate was centrifuged at 10,000 rpm for 30 minutes. The supernatant liquid was lyophilized. The lyophilized substance was dissolved in 1 ml of water, and the solution was processed for separation and purification by HPLC equipped with a reversed-phase partition column (TSK gel ODS-120T) made by Toyo Soda Co., Ltd. Separation and purification was carried out ten times in the total using one-tenth each of the above-mentioned aqueous solution. The fractions of the same compound obtained in separate runs were combined together to yield a sample for NMR analysis. The column is 300 mm long and 7.8 mm in inside diameter, and the resin is 10 μm in diameter. The column temperature was kept at 40° C. and the elution system employed was a linear concentration gradient using a mixed solvent of 0.02% hydrochloric acid and acetonitrile, from 0.02% hydrochloric acid alone to 60% (v/v) acetonitrile, in such a manner that the content of acetonitrile increased at an increment of 1% (v/v) every minute, with a flow rate of 1.5 ml/min. After separation, the solvent was removed by using a lyophilizer or centrifugal evaporator. Thus, there were obtained four simple compounds Ia, Ib, Ic and Id.

After separation, the solvent was removed by using a lyophilizer or centrifugal evaporator. The resulting sample was analyzed by NMR in heavy water (D$_2$O) or deuterated dimethylsulfoxide (d$_6$-DMSO).

EXAMPLE 4

The same procedure as in Example 3 was repeated to *Nephila maculata* collected in Papua New Guinea to prepare a sample for NMR. NMR was run using heavy water (D$_2$O) or deuterated dimethylsulfoxide (d$_6$-DMSO).

Figure 3:
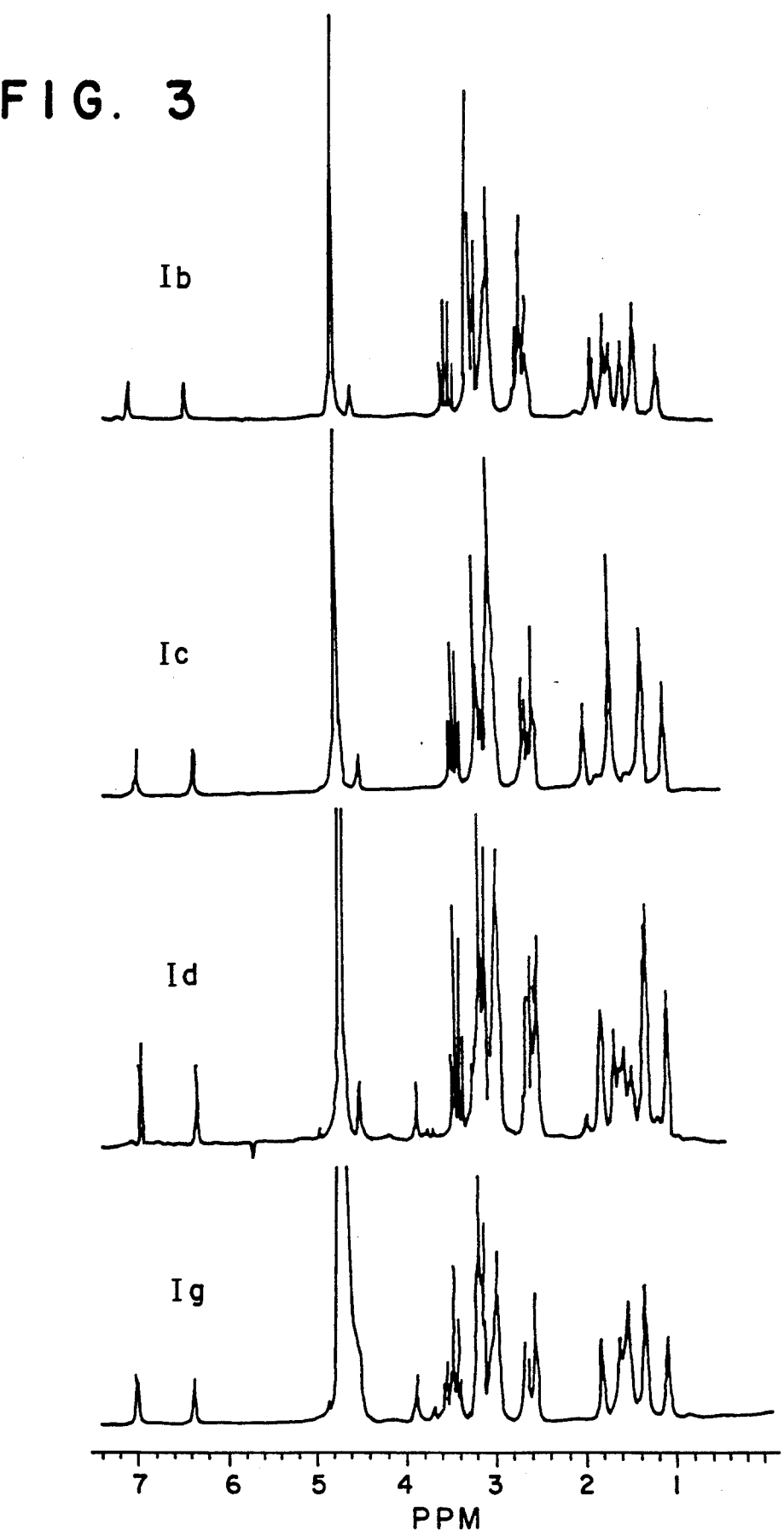
FIG. 3 shows proton NMR spectra of the compounds

The proton NMR spectra of Ib, Ic, Id and Ig in D$_2$O are shown in FIG. 3. The proton NMR spectra of Ig in D$_2$O and d$_6$-DMSO are compared in FIG. 4. The proton-COSY-NMR spectrum of Ig in d$_6$-DMSO is shown in FIG. 5.

The NMR spectrometry was performed using GX270 or GX400 made by Nippon Denshi Co., Ltd. or WH270 (equipped with ASPECT 2000) or AM 400 (equipped with ASPECT 3000) made by BRUKER Co., Ltd.

The compound Ig has molecular weight of 664 according to the fast atom bombardment mass spectrum (FAB-MASS) obtained by using DX-303 made by Nippon Denshi Co., Ltd. In the spectrum, a peak was noticed at M+H$^+$: m/z 665.

The compound Ig gave a UV spectrum (measured in a 50:50 (v/v) mixture of 0.02% hydrochloric acid and acetonitrile) which has the adsorption maximum at below 210 nm and at 280 nm. It emitted natural fluorescence (315 nm) upon exposure to an excitation light (280 nm).

EXAMPLE 5 wettable powder

A wettable powder was prepared according to the following formulation.

| | |
|---|---|
| Compound Ic | 0.001 wt % |
| Sodium ligninsulfonate | 9.999 wt % |
| Nonipol ® - 85 | 10 wt % |
| Clay | 80 wt % |

EXAMPLE 6 dust

A dust was prepared according to the following formulation.

| | |
|---|---|
| Compound Ic | 0.0001 wt % |
| Clay | 99.9999 wt % |

TEST EXAMPLE

Five young larvae of *Culex pipiens molestus* were placed in a glass test tube, 6 mm in diameter, containing 0.2 ml of aqueous solution of the compound Ic in a concentration of 50 μg/ml. Three hours later, the number of poisoned and dead larvae was counted. This test was duplicated. The results are shown below. Incidentally, the sample solution was replaced by 0.2 ml of water in control in place of 0.2 ml of aqueous solution of the compound Ic of 50 μg/ml.

Ration of poisoned and dead larvae:

| | |
|---|---|
| Compound Ic | 40% |
| Control | 0% |

We claim:
1. A purified compound of the formula:

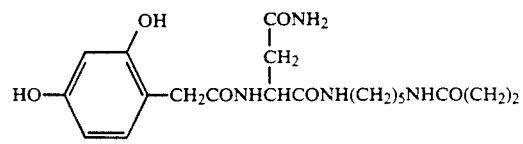

-continued

NH[(CH$_2$)$_m$NH]$_p$(CH$_2$)$_n$NHR where R represents a group of the formula:

—COCH(CH$_2$)$_3$NHC=NH
   |            |
   NH$_2$      NH$_2$ n represents 4 and p represents 0, and whose proton NMR spectrum is shown as Ig in FIG. 3, or a salt thereof.

2. An insecticidal composition comprising a carrier and an insecticidally effective amount of a purified compound of the formula:

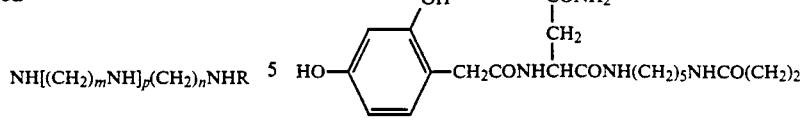

NH[(CH$_2$)$_m$NH]$_p$(CH$_2$)$_n$NHR wherein R represents a group of the formula:

—COCH(CH$_2$)$_3$NHC=NH
   |            |
   NH$_2$      NH$_2$ n represents 4 and p represents 0, and whose proton NMR spectrum is shown as Ig in FIG. 3, or a salt thereof.

3. A composition as set forth in claim 2, wherein said carrier is a liquid carrier and said compound is dissolved or dispersed in said liquid carrier.

4. A composition as set forth in claim 2, wherein said carrier is a solid carrier and said compound is mixed with or adsorbed on said solid carrier.

* * * * *